United States Patent [19]
Loeb

[11] 4,320,751
[45] Mar. 23, 1982

[54] CERVICAL CAP WITH FOAM LINING

[75] Inventor: Marvin P. Loeb, Chicago, Ill.

[73] Assignee: Contracap, Inc., Arlington Heights, Ill.

[21] Appl. No.: 122,541

[22] Filed: Feb. 19, 1980

[51] Int. Cl.³ .............................................. A61F 5/46
[52] U.S. Cl. ................................................... 128/127
[58] Field of Search .............. 128/127, 131, 150, 154, 128/285

[56] References Cited

U.S. PATENT DOCUMENTS

| | | | |
|---|---|---|---|
| 2,580,133 | 12/1951 | Sheen | 128/127 |
| 3,786,807 | 1/1974 | Dubin | 128/127 |
| 3,952,737 | 4/1976 | Lipfert et al. | 128/127 |
| 4,198,965 | 4/1980 | Strickman et al. | 128/127 |

*Primary Examiner*—C. Fred Rosenbaum

[57] ABSTRACT

A prefabricated cervical cap includes a generally domelike flexible shell of a depth sufficient to receive therein a major portion but not all of cervix uteri and a resilient, form-assuming internal liner for the shell. The liner is integral with the shell and is deformable upon contact with cervix uteri without substantial deformation of a contiguous portion of the cervix uteri. The liner may extend beyond the shell. In a preferred embodiment the cervical cap includes a one-way valve means that accomodates the flow of a uterine discharge without need to remove the cap.

22 Claims, 6 Drawing Figures

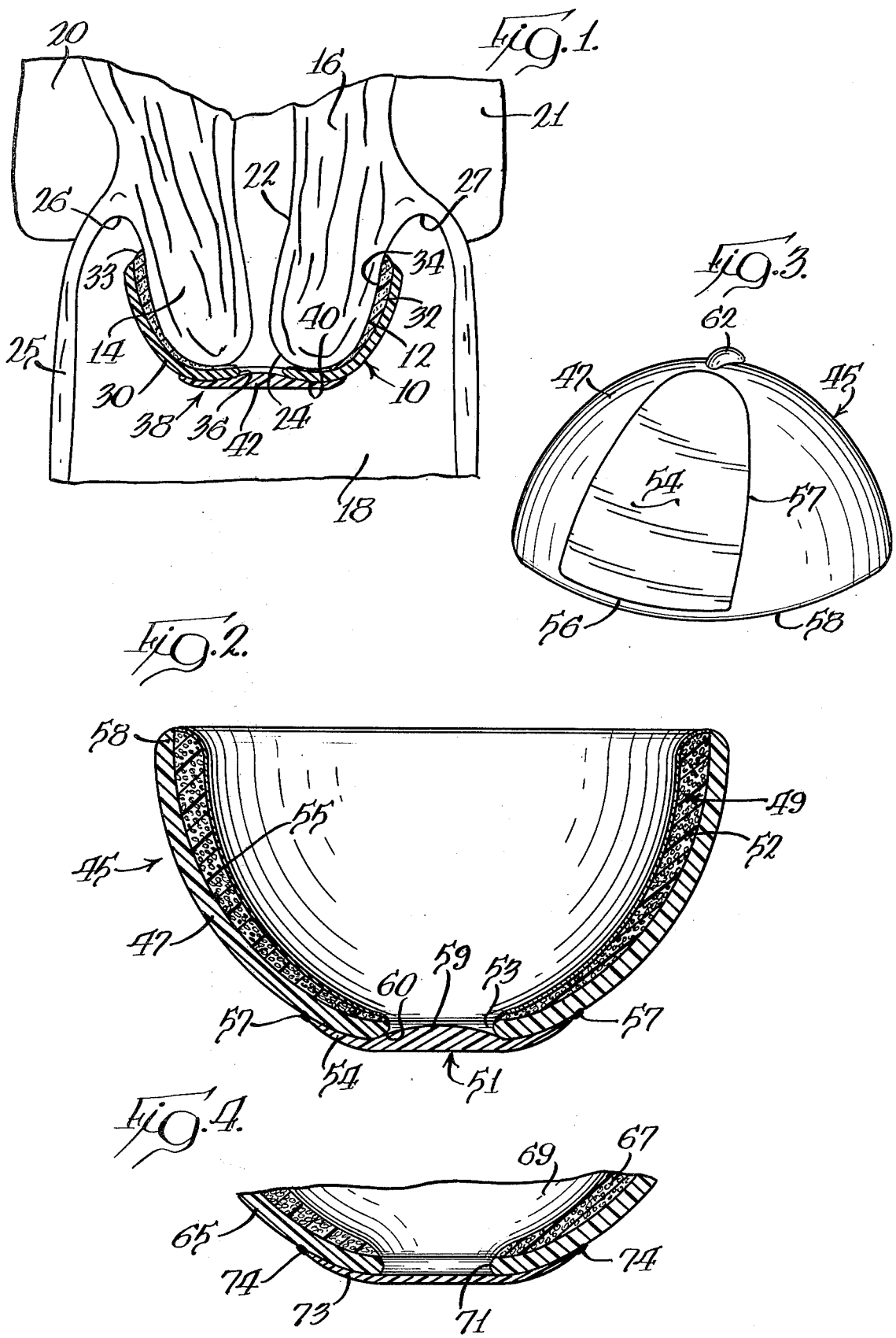

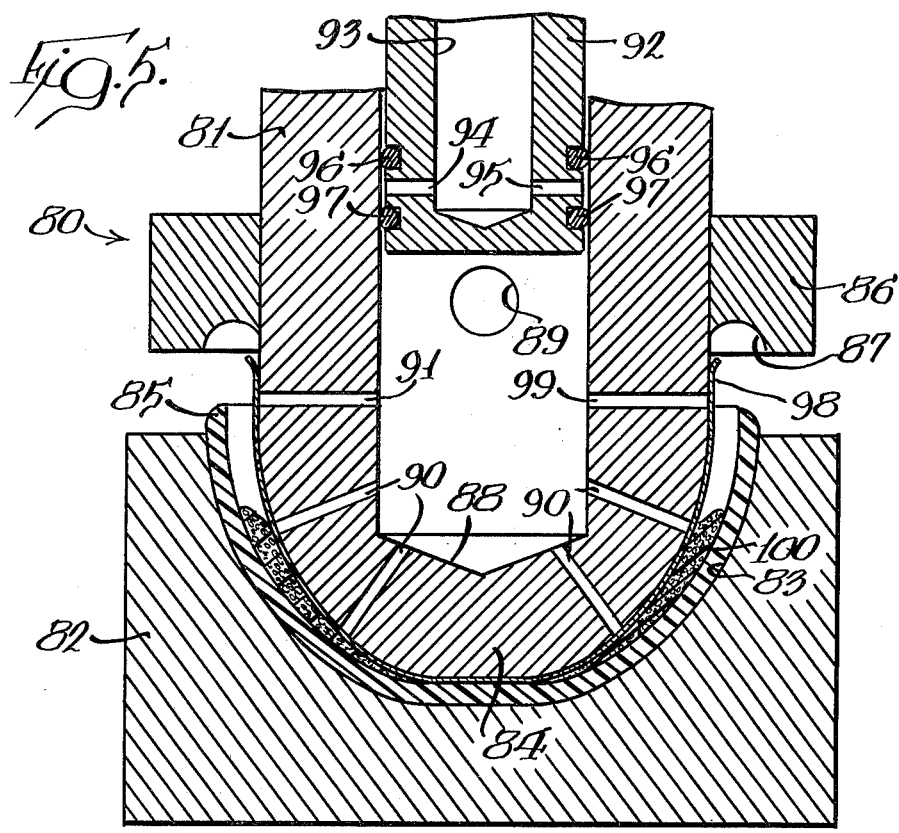
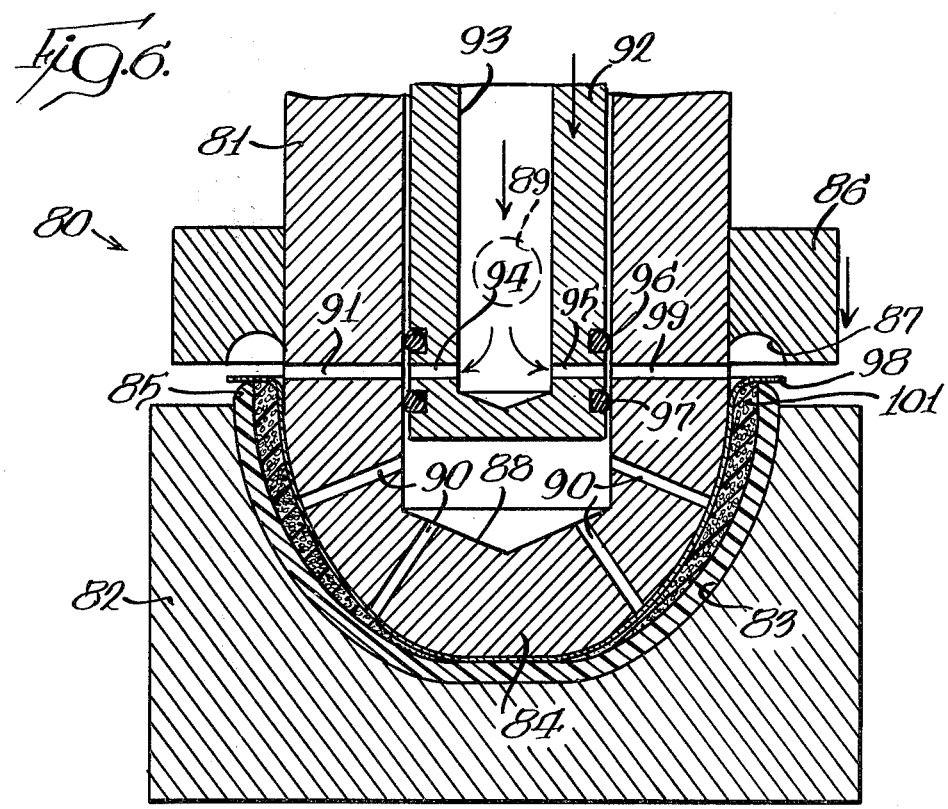

CERVICAL CAP WITH FOAM LINING

TECHNICAL FIELD

This invention relates to contraceptive devices and means for making such devices.

BACKGROUND OF THE INVENTION

Caps for cervix uteri as a birth control means have been known for many years and have been found among the artifacts of antiquity. It has been reported that Aetius of Amida suggested for this purpose the use of the skin of a pomegranate cut into a hollow cup, and that beeswax discs fashioned to fit over the cervix have been used in Europe.

Modern cervical caps comprise a pre-formed rubber cap that is positioned over the cervix uteri to act as a sperm barrier. Such caps are manufactured in several sizes to accommodate the various uterine sizes normally encountered; however, with such caps the fit for a particular individual is inexact and necessarily a compromise. Usually the cervix is either wedged into the cap or a compressive retaining means is utilized. As a result, these caps often become dislodged during normal body movement and particularly during coitus and have to be removed periodically to accommodate normal uterine discharges. Thus, such caps are inconvenient to use and have not achieved a high degree of reliability.

Premanufactured cervical caps with valves are also known and are shown in U.S. Pat. No. 2,836,177 to Sells, U.S. Pat. No. 3,952,737 to Lippert et al. and German Pat. No. 475,496 to Leopold. These caps also suffer from the aforementioned lack of stability and are subject to dislodgment during use.

U.S. Pat. No. 4,007,249 to Erb describes a technique for custom fabrication of a cervical cap having a value that is inserted during manufacture. The manufacturing expedients disclosed in this particular patent contemplate the painting of a liquid, polymerizable elastomeric material onto the cervix uteri followed by the polymerization of the painted material or, in the alternative, the use of a mold which retains a liquid, polymerizable elastomeric material in contact with the exocervical surface until it is polymerized.

The former expedient is impractical because the surface to which the liquid, polymerizable material is applied is wet with mucus and quite slippery, thus the applied material would fall off the exocervical surface due to gravity before polymerization of the material could take place and, in any event, it would be impossible to control the thickness of the applied polymerizable material during in situ polymerization. A cervical cap having a relatively non-uniform thickness is undesirable, however, because it is unstable and is likely to be dislodged in use. The second expedient disclosed in the Erb patent would also produce caps having an undesirable variable cap thickness that is likely to bring about dislodgment.

A further shortcoming of the caps shown in the Erb patent is that the prefabricated valving means utilized are of the leaflet or flap type. In such valves a viscous droplet of cervical mucus could hold the valve in an open position for an undesirably long time period, thereby providing an access aperture for sperm and defeating the very purpose of the cap. Moreover, inasmuch as the polymerizable material of the cap is in a fluid state when it surrounds the prefabricated valve, some of the fluid material may become enmeshed with the valve and interfere with its intended valving action after the material has polymerized.

U.S. Pat. No. 4,007,249 to Erb also mentions a technique disclosed initially by F. A. Wilde in 1838 in *Das Weibliche Gebar-Unvermogen* according to which a cervical cap allegedly can be made from a special wax impression of the vaginal portion of the cervix. As recognized by Erb, such a technique cannot produce an identical, negative image, cervix-conforming inside surface because the cervix would be deformed while the wax impression is being made. The uterus is suspended in the lower abdomen by ligaments, is easily movable, and would tend to move up into the abdomen even with a gentle force applied to the cervix. As a result, accurate registration would be prevented by such a movement with attendant lack of stability for the cervical cap produced in such manner.

The techniques described by Erb are also likely to suffer from the same drawback, albeit for a different reason. In particular, in practicing these techniques the vaginal wall has to be expanded using a vaginal speculum or similar implement in order to expose the cervix during cap molding. This expedient tends to distort the cervix as well, elongating it along an imaginary line between the tips of the inserted, open vaginal speculum blades and shortening the cervix along an imaginary line at right angles to the imaginary line between the tips of the speculum blades. The attendant cervical distortion exceeds the limits for prosthetic stability of the cervical cap that is produced.

Accordingly, while a stable, well-fitting cervical cap can be an effective birth-control device, heretofore it has not been possible to produce a cervical cap that has the requisite stability against dislodgment and that can be worn for extended periods of time such as months, or even years, without removal.

SUMMARY OF INVENTION

The present invention contemplates a non-invasive birth control device in the form of a pre-fabricated, removable cervical cap having a soft, flexible inner liner that conforms to the exocervical surface of cervix uteri in contact therewith to provide a cap-retaining fit therebetween. The lined cervical cap, in essence, "caps" the cervix uteri, the neck of the uterus protruding into the vagina, and is held in place by surface tension of mucous discharge that substantially continuously flows from the cervical os and passes between the inner surface of the cervical cap and the exocervical surface contiguous therewith. The flexible liner also substantially accommodates the usual cyclical configurational changes that the uterus, and thus its cervix, undergo. While the cervical cap of the present invention need not have a one-way valve means if worn temporarily or for relatively short time periods, a one-way valve means can be provided at the apex of the cervical cap so as to accommodate larger volume uterine discharges, such as menstrual flow, thereby permitting a longer uninterrupted wearing period for the cervical cap.

A prefabricated cervical cap embodying the present invention comprises a generally dome-like flexible shell and a resilient, form-assuming internal liner. The flexible shell is of sufficient depth to receive therein a major portion but not all of the cervix uteri. The resilient, form-assuming internal liner is integral with the shell and lines at least a major portion, and preferably all, of the inner shell surface about the periphery thereof. To maximize the effect of the mucus surface tension the area of intimate contact between the cap and the cervix uteri should be maximized and to this end it is preferable to maximize the available surface of the form-assuming internal liner. The liner may also extend beyond the shell to further increase the available contact area.

The liner is readily deformable upon contact with the cervix uteri without substantial deformation of contiguous portion of the cervix uteri, i.e., the liner has a lower hardness value (is softer) than the body tissue in contact therewith when the cap is in place. The cervical caps embodying the present invention can be fabricated in various sizes having diameter and depth dimensions sufficient to accommodate the usual uterine size variations.

BRIEF DESCRIPTION OF THE DRAWINGS

In the drawings,

FIG. 1 is an elevational view, partly in section, of a portion of the internal organs of the human female reproductive system with a cervical cap embodying the present invention in place;

FIG. 2 is an enlarged sectional view of another valved cervical cap embodying the present invention;

FIG. 3 is an enlarged perspective view of a valved cervical cap embodying the present invention;

FIG. 4 is a fragmentary sectional view of a valved cervical cap embodying the present invention and illustrating yet another one-way valve construction; and FIGS. 5 and 6 are sectional elevational views illustrating a device suitable for manufacturing a cervical cap embodying the present invention and the operation thereof.

DESCRIPTION OF PREFERRED EMBODIMENTS

Referring to FIG. 1, valved cervical cap 10, embodying the present invention, is shown positioned on exocervical surface 12 of cervix uteri 14, i.e., on the portio vaginalis cervicis or that portion of uterus 16 that protrudes into vagina 18. Uterus 16 is supported by broad ligaments 20 and 21, and defines fundus 22 that terminates in cervical os 24. Vaginal wall 25 together with cervix 14 define the fornices vaginae, i.e., lateral fornices 26 and 27 as well as the anterior and posterior fornices (not shown).

Cervical cap 10 includes a cup-shaped or dome-like shell 30, fabricated of a flexible material such as rubber, synthetic rubber, an elastomeric synthetic polymer, or the like, and a resilient foam lining 32 about the periphery of the inner concave surface of shell 30. Foam lining 32 can cover all or a major portion of the inner surface of shell 30. Foam lining 32 can terminate at about the rim of shell 30; however, lining 32 may also extend beyond the rim as shown in FIG. 1, thus providing additional contact area for contact with cervix 14 as well as a readily deformable band 33 that surrounds the rim of shell 30. The rim of shell 30 should not extend into the fornices as will be discussed in greater detail hereinbelow.

Foam lining 32 is soft and pliant, and has a hardness value that is lower than that of cervix 14. In this manner, when lining 32 contacts exocervical surface 12 as cap 10 is positioned onto cervix 14, lining 32 is deformed by cervix 14 to assume a mating configuration with exocervical surface 12. Stated in another way, the outer surface 34 of lining 32 is substantially complementary with exocervical surface 12 when cap 10 is in place.

In this manner a mucous discharge from uterus 16 is channeled between exocervical surface 12 and lining 32 as a thin film, and the surface tension of the mucus holds cap 10 firmly in place. To avoid absorption of mucus within foam lining 32, a smooth membrane or integral skin is provided on the outer surface 34 thereof.

If it is intended to wear cap 10 for extended periods of time, e.g., for time periods of about one month or longer, a provision is made to accommodate relatively larger volumes of uterine discharge such as menstrual flow. To this end aperture 36, covered with elastomeric web 38 is provided at about the apex of shell 30. Aperture 36 is defined by shell 30 so as to be adjacent to cervical os 24 when cap 10 is in place. Elastomeric web 38 is integral with shell 30 and together with the covered outer surface portion 40 of shell 30 provides a one-way valve means that communicates with aperture 36 and defines a channel for unidirectional flow in the direction away from cervical os 24 and through aperture 36, but not in the reverse direction. For enhanced valving action, elastomeric web 38 can be provided with protuberance or button 42 that extends into aperture 36 and seats against the inner edge surface of shell 30 that defines aperture 36. Protuberance 42 can be unitary with web 38 or can be initially separately formed and then bonded to web 38 so as to be integral therewith. However, a flap valve utilizing a web of substantially uniform thickness as illustrated in FIG. 4 is also suitable.

The above-described one-way valve means opens under increased, predetermined uterine pressure, usually at a pressure of about 10 to about 15 millimeters of mercury, and, when open, permits the passage of fluids such as mucus, menstrual flow, and the like, therethrough without disturbing the positioning of cervical cap 10 and while preventing the entry of sperm into fundus 22.

Another embodiment of the present invention is illustrated by valved cervical cap 45 shown in FIG. 2. In this particular embodiment, cap 45 includes flexible outer shell 47, foam inner liner 49, and one-way valve means 51. Foam inner liner 49 comprises foam layer 52 bonded to shell 47 on one side and to relatively thin, soft and flexible liner membrane 55 on the other. Foam layer 52 is thicker at rim 58 of outer shell 47 and gradually tapers down in thickness as layer 52 extends deeper into shell 47. However, to accommodate some cervix contours it may be desirable to have the foam lining of substantially uniform thickness throughout or even thicker at the apex of the shell. In the embodiment illustrated in FIG. 2, foam layer 52 extends from the rim of shell 47 to about aperture 53 at the apex of shell 47. Preferably, the thickest region of layer 52 it is thicker than the outer shell 47.

One-way valve means 51 comprises relatively thin, elastomeric membrane 54 peripherally bonded to the outer convex surface of shell 47 along the major portion of web periphery so as to define a tapered pocket overlying aperture 53 and thus a channel terminating in discharge port 56 (FIG. 3) near rim 58 of shell 47. In FIGS. 2 and 3 bead 57 delineates the bond between web 54 and shell 47. Discharge port 56 is spaced from aperture 53, preferably by at least one aperture diameter and, more preferably, is situated at or near rim 58 of shell 47. Most preferably discharge port 56 is situated at or no more than about 1 to about 3 millimeters away from rim 58. Elastomeric membrane or web 54 preferably is provided with unitary protuberance 59 that extends into aperture 53 and seats against edge 60 of shell 47 defining the aperture. Preferably edge 60 and the juxtaposed surface of protuberance 59 are oppositely chamfered so as to increase the area of sealing contact between protuberance 59 and edge 60.

To avoid dislodgment of the cervical cap such as cap 10 or cap 45 during momentary but relatively severe uterine displacement, it is important that the outermost edge of the cap, defined by rim 58 (FIG. 2), is sufficiently elastic to remain in contact with that portion of exocervical surface that is contiguous therewith even during such momentary displacement. To this end, it is desirable that the outermost edge of the cap be feathered, i.e., beveled or tapered as shown in FIGS. 1 and 2. The feathered outermost edge of the cap can also be provided with a plurality of peripheral cuts to form a clipped or frilled edge.

Tactile orientation marker 62 (FIG. 3) in the form of a protuberance or a discernible depression can be provided for facilitating orientation of valved cap 45 upon insertion so as to position discharge port 56 in or near the posterior fornix.

Shell 47, and thus cap 45, can be prefabricated in various standard sizes to accommodate the normally-encountered cervical configurations. For any given cervix, or range of cervices, shell 47 is dimensioned so as to have a diameter and depth sufficient to receive a major portion of the portio; however, the rim of shell 47 should terminate short of the fornices vaginae so as to guard against dislodgment of the cervical cap during activity that may cause the uterus to shift position and/or distend the normal configuration of the fornices. On the other hand, the readily deformable band of the cap inner liner that projects beyond the rim of shell 47 may extend into the fornices since any substantial deformation or distortion of the fornices will also bring about a corresponding complementary deformation of the produced deformable band, without causing the cap to be dislodged.

Another type of valved cervical cap embodying the present invention is shown in FIG. 4. In this particular embodiment the entire inner concave surface of shell 65 is lined with flexible foam liner 67 having a smooth, unitary skin 69. Aperture 71 is provided in shell 65 at the apex thereof. Elastomeric web 73 covers aperture 71 and is bonded to the outer, convex surface of shell 65 in a manner similar to that for web 54 in FIG. 3, i.e., a fan-shaped web is secured over aperture 71 and is bonded to shell 65 along bead 74 so as to define a pocket or channel and a discharge port at or near the rim of the cap. Web 73 is of substantially uniform thickness.

In use, the valved cervical caps embodying the present invention are positioned on the cervix so that the valve discharge port or external opening defined by the aperture-overlying elastomeric web in conjunction with the convex outer surface of the shell is located in or near posterior fornix. Such an arrangement results in a manifold increase in the distance that any sperm deposited in the vagina must travel in order to reach the cervical os.

Referring back to FIG. 1, a portion of the increased distance for sperm travel is in vagina 18 where the environment is very inhospitable to sperm motility due to the relatively low ambient pH. Usually sperm can survive in the vaginal vault only for a time period of about one to two hours. Inasmuch as sperm can move at a velocity of about one to two millimeters per minute, the substantial increase in the distance that sperm must travel when a valved cervical cap embodying the present invention is in place alone markedly reduces the likelihood of fertilization. Sperm travel to cervical os 24 via the valve means provided in the cervical cap is possible, if at all, only in close proximity to the walls defining the valve means. In instances where the shell portion of the cervical cap, or both the shell portion and the elastomeric web bonded thereto, are made of a thermoplastic elastomeric material, which materials exhibit an inhibitory effect on sperm motility, the likelihood of sperm reaching the cervical os 24 is further reduced.

The shell portion of the cervical cap embodying the present invention can be made from a wide variety of flexible materials such as natural rubber, silicone rubber, thermoplastic elastomers, and the like. The preferred materials of construction for this purpose are thermoplastic elastomers such as polyolefin blends, styrene/elastomer block copolymers, copolyesters, and polyurethane block copolymers. While these thermoplastic elastomers differ chemically, their morphology is similar. Blocks or domains of relatively hard thermoplastic constituents link elastomeric constituents in a network that behaves like a chemically crosslinked rubbery structure. At forming temperatures the relatively hard thermoplastic domains of the structure soften and allow the polymeric material to flow. Upon cooling, these relatively hard domains resolidify and re-establish the rubber-like, elastic structure.

Thermoplastic elastomers that exhibit a surface charge provide a further advantage for the present purposes in that the presence of such a charge on the fabricated shell and/or web tends to inhibit sperm motility.

For purposes of the present invention, the shell materials particularly suitable are the styrene/elastomer block copolymers such as those commercially available from the Shell Chemical Company, Oak Brook, Ill., under the designation "Kraton" and "Kraton G" and described in U.S. Pat. No. 3,231,635 to Holden et al. These styrenic thermoplastic elastomers are block copolymers of polystyrene and an elastomer such as polyisoprene, polybutadiene, ethylene-propylene, or ethylene-butylene rubber.

While thermoplastic elastomeric materials of varying hardness may be used to fabricate the shell portion of the cap, for optimum stability against dislodgment preferably the material should be harder than the cervical tissue that comes in contact therewith, yet the hardness should not be so high as to cause discomfort to the wearer or her consort. Preferably the shell material has a Shore A durometer hardness value of about 35 to about 70, and more preferably of about 45 to about 60. The shell material can be opaque, semi-transparent or transparent.

The web that forms a part of the one-way valve means can be made from the same elastomeric material or from a different elastomeric material, as long as the web can be secured to the shell in a convenient manner. For ease of manufacture it is preferred to have the web of the same elastomeric material as the shell material but thinner. The shell-to-web thickness ratio preferably is about 5:1 to about 15:1. In a typical cervical cap embodying the present invention the shell thickness is about 1 to about 4 millimeters and the web thickness is about 0.3 to about 0.5 millimeters.

The relative thicknesses of the shell and the integral web in each instance depend on a variety of factors such as the manufacturing procedure, forming temperatures, modulus of elasticity, and the like considerations. In general, however, the web thickness is selected so as to provide a valve-opening pressure of about 10 to about 15 millimeters of mercury for the one-way valve formed by the coaction of the web with the outer surface of the shell contiguous therewith.

The material for the web need not be thermoplastic as long as it exhibits the desired elasticity and can be secured to the shell. Not only heat sealing or ultrasonic bonding but other bonding means, e.g., adhesive bonding, can be utilized as well. In addition to the aforementioned thermoplastic elastomers, the web portion of the present valved cervical cap can be made from materials such as natural rubber, silicone rubber, polyurethanes, fluorocarbon rubbers, styrene-butadiene rubbers, and the like.

The inner foam lining can be made from a lightweight, rubbery foam such as a silicone elastomer foam, a flexible urethane foam, cross-linked polyethylene foam, and the like.

Suitable elastomeric silicone foams can be prepared by mixing an organohydrogensiloxane, a hydroxylated organosiloxane, and a platinum catalyst in amounts to provide a ratio of silicon-bonded hydrogen atoms to silicon-bonded hydroxyl radicals of about 2.5 to about 40 and thereafter permitting the mixture to foam. A detailed description of the preparation of foams of the foregoing type, as well as other suitable foams, is set forth in U.S. Pat. No. 3,923,705 to Smith et al. which description is incorporated herein by reference to the extent pertinent.

Suitable flexible urethane foams can be prepared by reacting relatively high molecular weight polyols with isocyanates.

For present purposes particularly suitable are the so-called high-resilient foams, i.e., foams having a sag factor of 2.7 and above, preferably a sag factor of about 3 to about 3.2. The expression "sag factor", as used herein and in the appended claims, denotes the ratio of the load needed to compress foam by 65% to the load needed to compress foam by 25%.

High-resilient polyurethane foams are prepared by reacting an isocyanate mixture constituted by about 80 percent 80/20 tolylene diisocyanate[1] and about 20 percent polymethylenepoly-phenyl isocyanate with a polyether triol having a molecular weight of about 4500 to about 6000 and made by reacting ethylene oxide with polypropylene oxide-based triols. Diol extenders such as methyldiethanol-amine, which also acts as a catalyst, can also be used in making high resilient foams.
[1] 80/20 refers to the ratio of the isomeric 2,4-tolylene diisocyanate to 2,6-tolylene diisocyanate.

The foam lining can be formed with an integral skin formed during the molding process, or a separate liner membrane can be provided. For the latter, the web materials discussed hereinabove in connection with the one-way valve means are suitable.

To manufacture a cervical cap embodying the present invention, first a flexible shell of predetermined configuration (with or without a valve means, as desired) is molded or otherwise fabricated. Thereafter a male mold or plug is positioned within the shell. The mold or plug is dimensioned so as to provide an annular space between the mold or plug face and the concave inner surface of the shell at least in the vicinity of the rim of the shell. The width of the annular space can vary; however, it is preferred that in the vicinity of the rim of the shell the annular space is at least as wide as the shell is thick. A predetermined amount of foamable material is then injected into the annular space and is permitted to foam in place, thereby forming the foam inner lining. The injected foamable material, as it rises in the annular space, structurally bonds itself to the inner shell surface and at the same time forms a relatively solid surface skin at the mold or plug face. The mold or plug face can be cooled, if desired, to suppress vaporization and/or expansion of the blowing agent contained in the foamable composition so that the foam expands at a much lower rate, if at all, at the mold surface.

For the fabrication of a cervical cap having a liner membrane over the foam layer within the shell, the assembling device shown in FIGS. 5 and 6 can be utilized. In particular, assembling device 80 comprises hollow movable mandrel 81 and stationary block 82 provided with cavity 83 adapted to receive distal end 84 of mandrel 81 therein. Cavity 83 is also dimensioned so as to receive therein a prefabricated, flexible cervical cap shell such as shell 85.

Mandrel 81 is surrounded by independently movable collar 86 slidably received thereon and having annular cavity 87 adapted to receive the rim portion of shell 85 as will be described in greater detail hereinbelow. Annular cavity is adjacent to mandrel 81 and faces distal end 84 thereof. Mandrel 81 further defines central, longitudinally-extending cavity 88 that communicates with a vacuum source (not shown) via passageway 89. Distal end 84 of mandrel 81 is provided with a plurality of passageways 90, 91 and 99 that are in communication with central cavity 88 and is dimensioned for entry into block cavity 83.

Situated within cavity 88 is hollow movable piston 92 having central passageway 93 in communication with a source of air under positive pressure (not shown). Through passageways 94 and 95 are provided in the distal end of piston 92. Spaced o-rings 96 and 97 are carried by piston 92, one on each side of passageways 94 and 95.

To begin fabrication of a cervical cap embodying the present invention, shell 85 is positioned in cavity 83. With piston 92 in the position shown in FIG. 5, prefabricated liner membrane 98 is held on distal end 84 by means of vacuum drawn through passageway 89 and is placed within shell 85 as shown. If desired, mandrel 81 can also be an ultrasonic horn and block 82 an anvil therefor, so that liner membrane 98 can be ultrasonically bonded to shell 85 as mandrel 81 is lowered into shell 85 and presses liner membrane 98 thereagainst.

Foamable substance 100 is introduced into the space between shell 85 and liner membrane 98, and foaming initiated in any convenient manner, e.g., by heating block 82, by catalytic action, or the like. After the foaming action has subsided and the produced foam layer extends substantially to the rim of shell 85 or beyond, piston 92 is moved downwardly within cavity 88 so as to seal off vacuum passageway 89 and to line up passageway 94 with passageway 91 and passageway 95 with passageway 99 as shown in FIG. 6. As a result, air under positive pressure is blown through the aligned passageways, urging the adjacent rim portion of liner membrane 98 away from mandrel 81. Thereafter collar 86 is brought down against block 82, in the process folding the aforementioned rim portion over foam layer 101 and bonding the rim portion to shell 85 and foam layer 101. Depending on the type of foamable material utilized, the adhesive properties of this material may be adequate to effect the desired bonding between liner membrane 98, foam layer 101 and shell 85. In the alternative, additional appropriate bonding agent may be applied to the surfaces that are to be bonded. If thermoplastic materials of construction are used, bonding may also be effected by heat sealing.

Next, mandrel 81 is elevated away from block 82, carrying the finished cap with it. Subsequent upward positioning of collar 86 and piston 92 with respect to distal end 84 "breaks" the vacuum in cavity 88 by opening passageways 91 and 99 to ambient atmosphere, thereby releasing the finished cap from mandrel 81.

The aforedescribed manufacturing procedure has been described with respect to the fabrication of a valve-less cervical cap in the interests of conciseness and clarity. However, it will be appreciated that the same expedient can be utilized to fabricate a valved cervical cap with but minor modifications to distal end 84 of the mandrel to accomodate the valve aperture. That is, distal end 84 is provided with an outwardly extending boss dimensioned to receive the opening in the liner membrane that corresponds to the valve aperture in the shell portion of the cap and also to enter within the valve aperture in the shell portion so as to properly orient the liner membrane and the shell with their respective apertures in registry.

The foregoing description and the accompanying drawings are intended as illustrative and are not to be taken as limiting. Still other variations and rearrangements of coacting parts within the spirit and scope of the present invention are possible and will readily present themselves to those skilled in the art.

I claim:

1. A non-invasive birth control device which comprises
an elastomeric cup for positioning over cervix uteri, having a substantially concave inner wall defining an aperture therein at the apex of the cup and substantially in alignment with the cervical os when the cup is positioned in place;
closure means associated with said cup and situated over said aperture to permit outflow of uterine discharge but prevent inflow of material into said cup through said aperture; and
a resiliently form-assuming inner liner member situated within said cup, integral with said concave wall, extending circumferentially about said wall, and defining a continuous inner cup surface portion for contacting the surface of portio vaginalis cervicis, said inner cup surface portion being more flexible than said concave wall.

2. The non-invasive birth control device in accordance with claim 1 wherein said inner liner member includes a layer of resilient foam.

3. The non-invasive birth control device in accordance with claim 2 wherein said resilient foam has a sag factor of at least about 2.7.

4. The non-invasive birth control device in accordance with claim 2 wherein said resilient foam has a sag factor of about 3 to about 3.2.

5. The non-invasive birth control device in accordance with claim 2 wherein said resilient foam layer is provided with an integral skin defining at least a major portion of the inner surface of said cup.

6. The non-invasive birth control device in accordance with claim 2 wherein said foam layer is covered with a flexible membrane defining at least a major portion of the inner surface of said cup.

7. The non-invasive birth control device in accordance with claim 2 wherein said layer of resilient foam extends beyond said shell.

8. The non-invasive birth control device in accordance with claim 1 wherein said closure means comprises an elastomeric web bonded to the cup external surface and defining a channel communicating with the aperture and terminating in a discharge port near the rim of the cup.

9. A prefabricated cervical cap which comprises a generally dome-like, flexible shell of sufficient depth to receive therein a major portion but not all of cervix uteri, a one-way valve means on the shell and defining a channel for substantially unidirectional flow in the direction away from the cervix uteri, and a resilient form assuming internal liner integral with said shell and peripherally lining at least a major portion of the inner surface of said shell, said liner comprising a resilient foam layer adjacent to said shell and a resilient, flexible membrane over the foam layer and defining at least a major portion of the cap inner surface.

10. The prefabricated cervical cap in accordance with claim 9 wherein the liner decreases in thickness toward apex of said shell.

11. The prefabricated cervical cap in accordance with claim 9 wherein the edge portion of the cap is feathered.

12. The prefabricated cervical cap in accordance with claim 9 wherein said resilient foam has a sag factor of at least about 2.7.

13. The prefabricated cervical cap in accordance with claim 9, wherein said flexible foam has a sag factor of about 3 to about 3.2.

14. The prefabricated cervical cap in accordance with claim 9 wherein said deformable liner extends beyond said shell.

15. The prefabricated cervical cap in accordance with claim 9 wherein the liner extends over the entire inner surface of said shell.

16. The prefabricated cervical cap in accordance with claim 9 wherein said one-way valve means is a flap valve.

17. A prefabricated cervical cap which comprises a generally dome-like, flexible shell of sufficient depth to receive therein a major portion but not all of cervix uteri, a resilient form assuming internal liner intergral with said shell and peripherally lining at least a major portion of the inner surface of said shell, and a one-way valve means at the apex of said shell, for accommodating outflow of uterine discharge but preventing inflow of material into said cap.

18. The prefabricated cervical cap in accordance with claim 10 wherein said shell and said internal liner define an aperture at the apex of the cap and wherein an elastomeric web extends over the aperture and is bonded to the shell external surface defining a channel communicating with the aperture and terminating in a discharge port near the rim of said shell.

19. The prefabricated cervical cap in accordance with claim 18 wherein said elastomeric web has a unitary protuberance that extends into the aperture.

20. The prefabricated cervical cap in accordance with claim 18 wherein said internal liner includes a layer of resilient foam that extends beyond said shell.

21. The prefabricated cervical cap in accordance with claim 18 wherein said internal liner includes a layer of resilient foam having a sag factor of at least about 2.7; a portion of said layer of resilient foam extending beyond said shell.

22. The prefabricated cervical cap in accordance with claim 18 wherein said internal liner includes a layer of resilient foam having a sag factor of about 3 to about 3.2; a portion of said layer of resilient foam extending beyond said shell.

* * * * *

UNITED STATES PATENT OFFICE
CERTIFICATE OF CORRECTION

Patent No. 4,320,751  Dated March 23, 1982

Inventor(s) Marvin P. Loeb

It is certified that error appears in the above-identified patent and that said Letters Patent are hereby corrected as shown below:

Col. 7, line 45, "polymethylenepoly-phenyl" should be -- polymethylenepolyphenyl --.

Col. 10, line 27, "flexible" should be -- resilient --.

Col. 10, line 50, "claim 10" should be -- claim 17 --.

Signed and Sealed this

Seventh Day of September 1982

[SEAL]

*Attest:*

*Attesting Officer*

GERALD J. MOSSINGHOFF

*Commissioner of Patents and Trademarks*